United States Patent [19]
Boualam et al.

[11] Patent Number: 5,382,597
[45] Date of Patent: Jan. 17, 1995

[54] ORGANO-TIN COMPOUNDS HAVING ANTI-TUMOUR ACTIVITY AND ANTI-TUMOUR COMPOSITIONS

[75] Inventors: Mohammad Boualam, Brussel; Marcel Gielen, Oppem; Abdelaziz El Khloufi, Brussel, all of Belgium; Dirk De Vos, Oestgeest, Netherlands; Rudolph Willem, Vilvoorde, Belgium

[73] Assignee: Pharmachemie B.V., Haarlem, Netherlands

[21] Appl. No.: 955,135

[22] Filed: Oct. 1, 1992

[30] Foreign Application Priority Data

Oct. 22, 1991 [EP] European Pat. Off. ........... 91202746

[51] Int. Cl.$^6$ .......................... A61K 31/22; C07F 7/22
[52] U.S. Cl. ...................................... 514/493; 556/94; 556/106; 556/108
[58] Field of Search .......................... 556/94, 106, 108; 514/493

[56] References Cited

U.S. PATENT DOCUMENTS 3,511,803   5/1970   Seki et al. .......... 260/45.75
4,043,949   8/1977   Treadwell et al. .......... 260/2.5 AC

FOREIGN PATENT DOCUMENTS 0119419   8/1987   European Pat. Off. .

OTHER PUBLICATIONS

Kieran C. Molloy et al, "Organotin Biocides. Part 11.[1] Triphenyltin Benzoates: Electronic versus Steric Control of Structure," *J. Chem Soc. Dalton Trans.*, pp. 1259–1266, (1988).

V. L. Narayanan, "Strategy for the Discovery and Development of Novel Anticancer Agents," *Structure–Activity Relationships of Anti–tumor Agents*, (1983).

W. D. Hohnick et al, "Synthesis of Tin(IV)–Oxygen and –Sulfur Heterocycles and Their Transformation to Tin(II) Analgoues," *Inorganic Chemistry*, vol. 18, No. 6, (1979).

Primary Examiner—José G. Dees
Assistant Examiner—Porfirio Nazarlo
Attorney, Agent, or Firm—Browdy and Neimark

[57] ABSTRACT

The invention relates to anti-tumor compositions containing as an active ingredient one or more compounds of the formula $$Ar_3Sn-O-C(O)-C_6H_2XYZ$$

wherein X and Y are each H, OH, halogen or alkyl; and Z is halogen, amino, alkoxy, acyloxy, sulphonic acid or alkyl. A number of these compounds are novel compounds.

5 Claims, No Drawings

ORGANO-TIN COMPOUNDS HAVING ANTI-TUMOUR ACTIVITY AND ANTI-TUMOUR COMPOSITIONS

This invention relates to novel organo-tin compounds having anti-tumour activity and to anti-tumour compositions.

In addition to platinum compounds, such as cis-platin, cis-$(NH_3)_2Cl_2Pt$, also organo-tin compounds are known anti-tumour drugs. An article by W. D. Honnick and J. J. Zuckermann, Inorg. Chem. 18, 1979, 1437–1443, "The Synthetis of Tin (IV) -Oxygen and Sulfur Heterocycles and their transformation to Tin (II) Analogues" describes a number of diorgano-tin compounds having anti-tumour activities, for instance

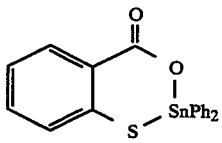

(A di-organo-tin compound is defined herein as a tin compound wherein two organic groups are bound directly to a Sn atom via carbon atoms).

In an article by V. L. Narayanan in "Structure-Activity Relationships of Anti-Tumor Agents", ed. D. N. Reinhoudt, T. A. Connors, H. M. Pinedo and K. W. van de Poll, Martinus Nijhoff, 1983, p. 16–33, it is reported that of 129 di-organo-tin compounds tested against P388 leukemia, 48% were found active, whereas of 132 tri-organo-tin compounds only 9% were found active.

The present invention provides anti-tumour compositions, containing as an active ingredient one or more compounds of the formula:

wherein Ar is a substituted or unsubstituted phenyl group; X and Y are each H, OH, halogen or alkyl; and Z is halogen, amino, alkoxy, acyloxy, sulphonic acid or alkyl; and pharmaceutically acceptable excipient.

Molloy et al, J. Chem. Soc. Dalton Trans. (1988), 1259–1266, disclose compounds of the formula

wherein X=2-$NH_2$, 2-$CH_3$, 2-$OCH_3$, 2-F, -3F, -4F, 2-Cl, 3-Cl, 4-Cl, 2-Br, 2-I (n=1) and 2,5-$Cl_2$, 3,4-$Cl_2$, 3,5-$Cl_2$, 2,4-$Cl_2$ (n=2). This article does not mention any pharmacological activity for these and related compounds.

EP-A-119419 discloses the compound $(C_6H_5)_3Sn-O-C(O)-C_6H_5OCOCH_3$ wherein the acetyl group is at the 2-position as a biocidal compound; a pharmacological activity is not mentioned. U.S. Pat. No. 4,043,949 concerns the use of triphenyltin-3-amino-2,5-dichlorobenzoate and other organotin-compounds as catalysts for the preparation of polyurethane foams. Again, no pharmacological activity is mentioned.

Preferably, the alkyl group is isopropyl. The preset compounds can be prepared by reacting triphenyltin hydroxide with $XYZC_6H_2COOH$ at elevated temperature.

PREPARATION

In all preparations, 2 g (5.4 mmol) of triphenyltin hydroxide was added to a solution of 5.4 mmol $XYZC_6H_2COOH$ in a mixture of 150 ml of toluene and 50 ml of ethanol. This mixture is heated at reflux for 6 hours; first the ternary azeotrope water/toluene/ethanol is distilled off using a Dean-Stark funnel, followed by half of the reining solvent. The obtained solution is evaporated under vacuum. An oily compound is obtained; this material is crystallized from ethanol or from $CH_2Cl_2$/petroleum ether.

The following compounds were prepared:

Triphenyltin ortho-methoxybenzoate, Compound 1 recrystallized from ethanol; m.p.: 102°–103° C.; yield: 68%; Rf on Polygram$^R$ SIL G/UV$_{254}$ TLC plates from Macherey-Nagel+CO, elution with cyclohexane/dioxane 1/1:0.80; Mössbauer parameters (in mm/s: quadrupole splitting QS:2.33, isomer shift IS: 1.22, band widths $\Gamma_1$ & $\Gamma_2$: 0.92 & 0.90; $^1$H NMR (CDCl$_3$) parameters (proton number: multiplicity, chemical shift in ppm [coupling constants in Hz]: H-3: d, 6.94 [8]; H-4: dd, 6.95 [7, 7]; H-5: hidden under the signals of meta and para protons; H-6: dd, 7.98 [8, 2]; ortho-H: m: 7.78–7.82; meta- & para-H: m: 7.39–7.46; CH$_3$O: s, 3.88.

Triphenyltin para-fluorbenzoate, Compound 2 recrystallized from ethanol; m.p.: 86°–87° C.; yield: 24%; Rf on Polygram$^R$ SIL G/UV$_{254}$ TLC plates, elution with petroleum ether/acetic acid 6/1:0.51; Mössbauer parameters (in mm/s): QS:2.54, IS: 1.27, $\Gamma_1$ & $\Gamma_2$: 0.85 & 0.86; $^1$H NMR (CDCl$_3$) parameters: H-2 & H-6: dd, 8.14 [9, 6]; H-3 & H-5: dd, 7.05 [9, 9]; ortho-H: m: 7.76–7.81; meta- & para-H: m:7.45–7.51.

Triphenyltin 3,5-difluorobenzoate, Compound 3 recrystallized from ethanol; m.p.: 121°–122° C; yield: 30%; Rf on Polygram$^R$ SIL G/UV$_{254}$ TLC plates, elution with cyclohexane/dioxane 1/1:0.53; Mössbauer parameters (in mm/s): QS:2.61, IS: 1.26, $\Gamma_1$ & $\Gamma_2$: 0.90 & 0.89; $^1$H NMR (CDCl$_3$) parameters: H-2 & H-6: dd, 7.62 [8, 2]; H-4: tt, 6.94 [9, 2]; ortho-H: m: 7.76–7.82; meta- & para-H: m: 7.45–7.51.

Triphenyltin acetylsalicylate, Compound 4 recrystallized from CH$_2$Cl$_2$/petroleum ether; m.p.: 110°–111° C.; yield: 85%; Rf on Polygram$^R$ SIL G/UV$_{254}$ TLC plates, elution with cyclohexane/dioxane 1/1: 0.85; Mössbauer parameters (in mm/s): QS: 2.54, IS: 1.27, $\Gamma_1$ & $\Gamma_2$: 0.86 & 0.89; $^1$H NMR (CDCl$_3$) parameters: CH$_3$:s: 2.04; H-3: dd: 7.04 [8,1]; H-4: ddd: 7.23 [8, 8, 1]; H-6: dd: 8.11 [8,2]; ortho-H: m: 7.64–7.90 [$^3$J(Sn—H)=60]; H-5, meta- & para-H: m:7.35–7.50.

Triphenyltin 5-chlorosalicylate, Compound 5 recrystallized from CH$_2$Cl$_2$/petroleum ether; m.p.: 122°–123° C.; yield: 75%; Rf on Polygram$^R$ SIL G/UV$_{254}$ TLC plates, elution with cyclohexane/dioxane 1/1: 0.76; Mössbauer parameters (in mm/s): QS: 2.79, IS: 1.32, $\Gamma_1$ & $\Gamma_2$: 0.90 & 0.89, $^1$H NMR (CDCl$_3$) parameters: H-3: d: 6.88 [9]; H-6: d: 7.94 [2]; ortho-H: m: 7.65–7.90 [$^3$J(Sn—H)=64]; H-4 meta- & para-H: m: 7.45–7.53; OH: bs: 11.06.

Triphenyltin 5-aminosalicylate, Compound 6 recrystallized from CH$_2$Cl$_2$/petroleum ether; m.p.: 145°–146° C.; yield: 78%; Rf on Polygram$^R$ SIL G/UV$_{254}$ TLC plates, elution with cyclohexane/dioxane 1/1: 0.73; Mössbauer parameters (in mm/s): QS: 3.10, IS: 1.30, Γ$^1$ & Γ$_2$: 0.90 & 0.89; $^1$H NMR (CDCl$_3$) parameters: H-3 & H-4: AB part of an ABX system with V$_A$=6.75, V$_B$ 6.79, J$_{AB}$=9, J$_{AX}$=nv and J$_{BX}$=2; H-6: d:7.292 [2]; ortho-H:m:7.64–7.90 [$^3$J(Sn—H)=54];meta- & para-H: m:7.40–7.50; NH$_2$: m: 2.71–3.42; $^{13}$C NMR (CDCl$_3$): ipso-C: 137.7 [$^1$J(Sn—C)=630]; ortho-C: 136.7 [$^2$J(Sn—C)=47]; meta- C: 128.9 [$^3$J(Sn—C)=64]; para-C: 130.3; C-1: 113.1;C-2: 154.8; C-3: 116.5; C-4: 124.0; C-5: 137.9; C-6: 117.6; CO: 174.8; $^{119}$Sn NMR (CDCl$_3$): −116.1.

Triphenyltin 5-methoxysalicylate, Compound 7 recrystallized from CH$_2$Cl$_2$/petroleum ether; m.p.: 137°–138° C.; yield: 72% Rf on Polygram$^R$ SIL G/UV$_{254}$ TLC plates, elution with cyclohexane/dioxane 1/1:0.97; Mössbauer parameters (in mm/s): QS: 2.75, IS: 1.28 Γ$_1$ & Γ$_2$: 0.91 & 0.90; $^1$H NMR (CDCl$_3$) parameters: CH$_3$O: s: 3.74; H-3: d: 6.864 [9]; H-4: dd: 7.024 [9.3]; ortho-H: m: 7.65–7.91 [$^3$J(Sn—H) s 63]; H-6, meta- & para-H: m: 7.42–7.53; OH: bs: 4.5; $^{13}$C NMR (CDCl$_3$): CH$_3$O: 55.8; ipso-C: 137.9 [$^1$J(Sn—C)=632]; ortho-C: 136.7 [$^2$J(Sn—C)=47]; meta-C: 128.9 [$^3$J(Sn—C)=62]; para-C: 130.3; C-1: 114.0; C-2: 156.0; C-3: 118.0; C-4: 123.5; C-5: 151.8; C-6: 113.1; CO: 174.7; $^{119}$Sn NMR (CDCl$_3$): −97.6

Triphenyltin 5-hydroxysulfonylsalicylate, Compound 8 recrystallized from ethanol; m.p.: >350° C.; yield: 76%; Rf on Polygram$^R$ SIL G/UV$_{254}$ TLC plates, elution with ethanol: 0.88; $^1$H NMR (DMSO-d$_6$) parameters: H-3: d: 6.818 (8); H-6: d: 8.105 [2]; ortho-H: d: 7.771 (7) [$^3$J(Sn—H)=106]; H-4, meta- & para-H: m: 7.34–7.46; OH: bs: 11.6, SO$_3$H: 3.39–3.47; $^{13}$C NMR (DMSO-d$_6$): ipso-C: 144.6; ortho-C: 139.5; meta-C: 133.6; para-C: 134.3; C-1: 118.3; C-2: 165.8; C-3: 121.2; C-4: 137.5; C-5: 152.9; C-6: 132.7; CO: 179.3; $^{119}$Sn NMR (DMSO-d$_6$): −276.7

Triphenyltin 3,5-di-isopropylsalicylate, Compound 9 recrystallized from ethanol; m.p.: 150°–151° C.; yield: 90%; Rf on Polygram$^R$ SIL G/UV$_{254}$ TLC plates, elution with cyclohexane/dioxane 1/1: 0.78; m.p. >350° C.; yield 76%; Rf on Polygram$^R$ SIL G/UV$_{254}$ TLC plates, elution with ethanol: 0.88; Mössbauer parameters (in mm/s): QS: 2.56, IS: 1.28, Γ$_1$ & Γ$_2$: 0.86 & 0.92; $^1$H NMR (CDCl$_3$) parameters: 3-i-Pr: CH: sept: 3.344 [7]; CH$_3$: sept: 1.231 [7]; 5-i-Pr: CH: sept: 2.843 [7]; CH$_3$: sept: 1.220 [7]; H-4: d: 7.236 [2]; H-6; d: 7.715 [2]; ortho-H: m: 7.67 −7.91 [$^3$J(Sn—H)=59]; meta- & para-H: m: 7.40–7.49; $^{13}$C NMR (CDCl$_3$): 3-i-Pr; CH$_3$: 24.1; CH: 33.4; 5-i-Pr: CH$_3$: 22.4; CH: 26.9; ipso-C: 137.9 [$^1$J($^{119/117}$Sn-$^{13}$C)=648/618]; ortho-C: 138.0 [$^2$J(Sn—C)=48]; meta-C: 128.9 [$^3$J(Sn—C)=64]; para-C: 130.3 [$^4$J(Sn—C)=13]; C-1: 112.1; C-2: 157.4; C-3: 136.2; C-4: 130.6; C-5: 138.6; C-6: 125.9; CO: 175.7; $^{119}$Sn NMR (CDCl$_3$): −101.4

The above compounds were tested in vitro against the following human tumour cell lines:
MCF-7 mammary carcinoma (M cells)
WiDr colon tumour cells (W cells)

The tests were carried out according to the method of R. van Lambalgen and P. Lelieveld, the PIT method: an automated in vitro technique for drug toxicity testing. Invest. New Drug 5, 161–165 (1987).

The ID$_{50}$ values in ng/ml for the above nine compounds and for two known compounds (compounds 10 and 11) were determined according to the above-mentioned procedure. The ID$_{50}$ value is the amount which inhibits 50% of the cell growth. The results are shown in the following Table. (C$_6$H$_5$)$_3$Sn—O—C-(O)—C$_6$H$_2$XYZ

We claim:

| | | ID$_{50}$ values in ng/ml | | | |
|---|---|---|---|---|---|
| Compound | X | Y | Z | MCF-7 | WiDr |
| 1 | H | H | 2-OCH$_3$ | 16 | 15 |
| 2 | H | H | 4-F | 15 | 14 |
| 3 | H | 3-F | 5-F | 18 | 17 |
| 4 | H | H | 2-OC(O)CH$_3$ | 13 | 9 |
| 5 | H | 2-OH | 5-Cl | 11 | 18 |
| 6 | H | 2-OH | 5-NH$_2$ | 14 | 17 |
| 7 | H | 2-OH | 5-OCH$_3$ | 6 | 15 |
| 8 | H | 2-OH | 5-SO$_3$H | 100 | 131 |
| 9 | 2-OH | 3-CH(CH$_3$)$_2$ | 5-CH(CH$_3$)$_2$ | 8 | 13 |
| 10 | | | | 585 | 15800 |
| 11 (Cisplatin) | | | | 850 | 624 |

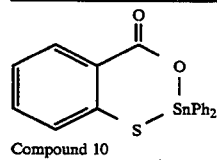

Compound 10

From the above results it can be seen that the preset tri-organo-tin compounds exhibit excellent ID$_{50}$ values which are considerably higher than the ID$_{50}$ values of the known compounds which were tested for comparative purposes.

1. A compound of the formula

Ar$_3$Sn—O—C(O)—C$_6$H$_2$XYZ wherein Ar is phenyl;
X and Y are each H, OH, halogen or alkyl; and
Z is halogen, amino, alkoxy, acyloxy, sulphonic acid or alkyl,
with the proviso that, when Z is alkoxy, acyloxy or alkyl, X and Y are not both H; when Z is amino, X and Y are both not H or chloro; when Z is halogen, X and Y are not both H, and one of X and Y is not halogen; and when Z is alkyl, and one of X and Y is OH, the other of X and Y is not alkyl or H.

2. A compound of the formula

Ar$_3$Sn—O—C(O)—C$_6$H$_2$XYZ wherein Ar is phenyl;
X and Y are each H, halogen or alkyl; and
Z is halogen, amino, alkoxy, acyloxy, sulphonic acid or alkyl,
with the proviso that, when Z is alkoxy, acyloxy or alkyl, X and Y are not both H; when Z is amino, X and Y are both not H or chloro; and when Z is halogen, X and Y are not both H, and one of X and Y is not halogen.

3. A method for the treatment of tumors comprising administering an effective amount of a compound of the formula

Ar$_3$Sn—O—C(O)—C$_6$H$_2$XYZ wherein Ar is phenyl;
X and Y are each H, OH, halogen or alkyl; and Z is a halogen, amino, alkoxy, acyloxy, sulphonic acid or alkyl.

4. A method in accordance with claim 3, wherein said tumor is a mammary carcinoma or a colon tumor.

5. In a method for the treatment of tumors which respond to treatment by organo-tin compounds comprising administering to a patient having such a tumor an effective amount of an organo-tin compound, the improvement wherein said organo-tin compound is a compound of the formula $$Ar_3Sn-O-C(O)-C_6H_2XYZ$$

wherein Ar is phenyl;
X and Y are each H, OH, halogen or alkyl; and
Z is a halogen, amino, alkoxy, acyloxy, sulphonic acid or alkyl.

* * * * *